US010398668B2

(12) United States Patent
Po

(10) Patent No.: US 10,398,668 B2
(45) Date of Patent: Sep. 3, 2019

(54) GLUTAMATE TREATMENT OF CARDIOVASCULAR DISORDERS

(71) Applicant: The Board of Regents of the University of Oklahoma, Norman, OK (US)

(72) Inventor: Sunny Po, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 33 days.

(21) Appl. No.: 15/686,727

(22) Filed: Aug. 25, 2017

(65) Prior Publication Data

US 2017/0348264 A1 Dec. 7, 2017

Related U.S. Application Data

(63) Continuation-in-part of application No. 14/104,422, filed on Dec. 12, 2013, now Pat. No. 9,744,235, which is a continuation-in-part of application No. 12/907,806, filed on Oct. 19, 2010, now Pat. No. 8,740,872.

(60) Provisional application No. 61/836,392, filed on Jun. 18, 2013.

(51) Int. Cl.
| | |
|---|---|
| *A61K 9/00* | (2006.01) |
| *A61K 9/51* | (2006.01) |
| *A61K 33/06* | (2006.01) |
| *A61K 9/50* | (2006.01) |
| *A61K 9/08* | (2006.01) |
| *A61K 31/197* | (2006.01) |
| *A61K 41/00* | (2006.01) |
| *A61K 33/02* | (2006.01) |
| *A61N 2/00* | (2006.01) |
| *B82Y 5/00* | (2011.01) |

(52) U.S. Cl.
CPC .......... *A61K 31/197* (2013.01); *A61K 9/0009* (2013.01); *A61K 9/0019* (2013.01); *A61K 9/08* (2013.01); *A61K 9/51* (2013.01); *A61K 9/513* (2013.01); *A61K 9/5115* (2013.01); *A61K 9/5146* (2013.01); *A61K 9/5153* (2013.01); *A61K 33/02* (2013.01); *A61K 33/06* (2013.01); *A61K 41/00* (2013.01); *A61N 2/00* (2013.01); *A61K 9/5094* (2013.01); *B82Y 5/00* (2013.01)

(58) Field of Classification Search
CPC ........ A61K 9/009; A61K 9/0019; A61K 9/08; A61K 9/51; A61K 9/5115; A61K 9/513; A61K 9/5146; A61K 9/5153; A61K 33/02; A61K 41/00; A61K 9/0021; A61N 2/00

See application file for complete search history.

(56) References Cited

U.S. PATENT DOCUMENTS

| | | | |
|---|---|---|---|
| 5,427,767 A | 6/1995 | Kresse et al. | |
| 5,705,195 A | 1/1998 | Volkonsky et al. | |
| 6,048,515 A | 4/2000 | Kresse et al. | |
| 6,200,547 B1 | 3/2001 | Volkonsky et al. | |
| 6,514,481 B1 | 2/2003 | Prasad et al. | |
| 6,743,779 B1 | 6/2004 | Unger et al. | |
| 6,977,080 B1 | 12/2005 | Donovan | |
| 7,485,624 B2 | 2/2009 | Donovan | |
| 7,709,440 B2 | 5/2010 | Shaari | |
| 7,723,311 B2 | 5/2010 | Seeney et al. | |
| 7,731,977 B2 | 6/2010 | Ackerman | |
| 2005/0175703 A1 | 8/2005 | Hunter et al. | |
| 2006/0002852 A1 | 1/2006 | Saltzman et al. | |
| 2006/0025713 A1 | 2/2006 | Rosengart et al. | |
| 2006/0057211 A1 | 3/2006 | Chorny et al. | |
| 2006/0228421 A1 | 10/2006 | Seeney et al. | |
| 2007/0191895 A1* | 8/2007 | Foreman ........... | A61N 1/36114 607/14 |
| 2007/0196281 A1 | 8/2007 | Jin et al. | |
| 2008/0241262 A1 | 10/2008 | Lee et al. | |
| 2009/0082611 A1 | 3/2009 | Levy et al. | |
| 2009/0216320 A1 | 8/2009 | Levy et al. | |
| 2009/0226521 A1 | 9/2009 | Smyth et al. | |
| 2009/0287036 A1 | 11/2009 | Shapiro et al. | |
| 2010/0036480 A1 | 2/2010 | Viller et al. | |
| 2010/0079142 A1 | 4/2010 | Fontius | |
| 2010/0204674 A1 | 8/2010 | Forbes et al. | |

OTHER PUBLICATIONS

Weissleder, et al.; "Superparamagnetic Iron Oxide: Pharmacokinetics and Toxicity," AJR (1989), vol. 152, pp. 167-173.
Forbes et al., "An Approach to Targeted Drug Delivery Based on Uniform Magnetic Fields," IEE Transactions on Magnetics (2003), vol. 39, No. 5, pp. 3372-3377.
Douziech-Eyrolles et al., "Nanovectors for Anticancer Agents Based on Superparamagnetic Iron Oxide Nanoparticles," International Journal of Nanomedicine: (2007), vol. 2, No. 4, pp. 541-550.
Hou et al., "Ganglionated Plexi Modulate Extrinsic Cardiac Autonomic Nerve Input," Journal of the American College of Cardiology by the American College of Cardiology Foundation, Elsevier Inc. (2007), vol. 50, No. 1, pp. 61-68.
Forbes et al., "Validation of High Gradient Magnetic Field Based Drug Delivery to Magnetizable Implants Under Flow," IEEE Transactions on Biomedical Engineering (2008), vol. 55, No. 2, pp. 643-649.
Avilés et al., "Isolated Swine Heart Ventricle Perfusion Model for Implant Assisted-Magnetic Drug Targeting," International Journal of Pharmaceutics (2008), vol. 361, pp. 202-208.
Basak et al., "Transport Characteristics of Nanoparticle-Based Ferrofluids in a Gel Model of the Brain," International Journal of Nanomedicine (2009), vol. 4, pp. 9-26.

(Continued)

*Primary Examiner* — Edelmira Bosques
(74) *Attorney, Agent, or Firm* — Dunlap Codding, P.C.

(57) ABSTRACT

Compositions and methods for treating various cardiovascular disorders include targeted delivery of glutamate for impairing a targeted portion of the autonomic nervous system (ANS). Targeted delivery may be via direct injection into the targeted portion of the ANS or via vascular injection of magnetically-targetable nanoparticles.

18 Claims, 1 Drawing Sheet

(56) References Cited

OTHER PUBLICATIONS

Polyak et al., "Magnetic Targeting for Site-Specific Drug Delivery: Applications and Clinical Potential," Informa Healthcare, London (2009), vol. 6, No. 1, pp. 53-70.
Kumar et al., "Multifunctional Magnetic Nanoparticles for Targeted Delivery," Nanomedicine: Nanotechnology, Biology, and Medicine (2010), vol. 6, pp. 64-69.
Hoare et al., "A Magnetically Triggered Composite Membrane for On-Demand Drug Delivery," American Chemical Society, Nano Letters (2009), vol. 9, No. 10, pp. 3651-3657.
Chorny et al., "Targeting Stents With Local Delivery of Paclitaxel-Loaded Magnetic Nanoparticles Using Uniform Fields," PNAS (2010), vol. 107, No. 18, pp. 8346-8351.
Yu et al., "Autonomic Denervation Using Magnetic Nanoparticles," Heart Rhythm Society, Heart Rhythm Journal (2010), vol. 7, Issue 5S vol. 7, No. 5S, PO1-13.
Petros et al., "Strategies in the Design of Nanoparticles for Therapeutic Applications," Nature Reviews, Drug Discovery (2010), vol. 9, pp. 615-627.
Katritsis, et al.; "Autonomic Denervation Added to Pulmonary Vein Isolation for Paroxysmal Atrial Fibrillation," Journal of the American College of Cardiology (2013), vol. 62, No. 24, pp. 2318-2325.
Lu, et al.; "Autonomic Mechanism for Initiation of Rapid Firing From Atria and Pulmonary Veins: Evidence by Ablation of Ganglionated Plexi," Cardiovascular Research (2009), vol. 84, pp. 245-252.
Pukushalov, et al.; "Selective Ganglionated Plexi Ablation for Paroxysmal Atrial Fibrillation," Heart Rhythm (2009), vol. 6, No. 9, pp. 1257-1264.
Pukushalov, et al.; "Ganglionated Plexi Ablation for Longstanding Persistent Atrial Fibrillation," Europace (2010), vol. 12, pp. 342-346.
Yu, et al.; "Autonomic Denervation with Magnetic Nanoparticles," Circulation (2010), vol. 122, pp. 2653-2659.
U.S. Appl. No. 12/907,806 Kenneth J. Dormer, filed Oct. 19, 2010; Office Action dated Nov. 21, 2012; 14 pages.
U.S. Appl. No. 12/907,806 Kenneth J. Dormer, filed Oct. 19, 2010 Response to Office Action dated May 20, 2013; 18 pages.
U.S. Appl. No. 12/907,806 Kenneth J. Dormer, filed Oct. 19, 2010; Final Office Action dated Jul. 25, 2013; 17 pages.
U.S. Appl. No. 12/907,806; Kenneth J. Dormer, filed Oct. 19, 2010; Response to Final Office Action dated Aug. 29, 2013; 5 pages.
U.S. Appl. No. 12/907,806; Kenneth J. Dormer, filed Oct. 19, 2010; Notice of Allowance dated Sep. 9, 2013; 9 pages.
U.S. Appl. No. 14/104,422; Sunny Po, filed Dec. 12, 2013; Office Action dated Jul. 28, 2015; 11 pages.
U.S. Appl. No. 14/104,422; Sunny Po, filed Dec. 12, 2013; Response to Office Action dated Dec. 22, 2015; 11 pages.
U.S. Appl. No. 14/104,422; Sunny Po, filed Dec. 12, 2013; Final Office Action dated Mar. 9, 2016; 12 pages.
U.S. Appl. No. 14/104,422; Sunny Po, filed Dec. 12, 2013; Amendment and Response to Final Office Action dated Aug. 9, 2016; 11 pages.
U.S. Appl. No. 14/104,422; Sunny Po, filed Dec. 12, 2013; Office Action dated Sep. 13, 2016; 7 pages.
U.S. Appl. No. 14/104,422; Sunny Po, filed Dec. 12, 2013; Amendment and Response to Office Action dated Feb. 7, 2017; 6 pages.
U.S. Appl. No. 14/104,422; Sunny Po, filed Dec. 12, 2013; Notice of Allowance dated Apr. 27, 2017; 8 pages.

* cited by examiner

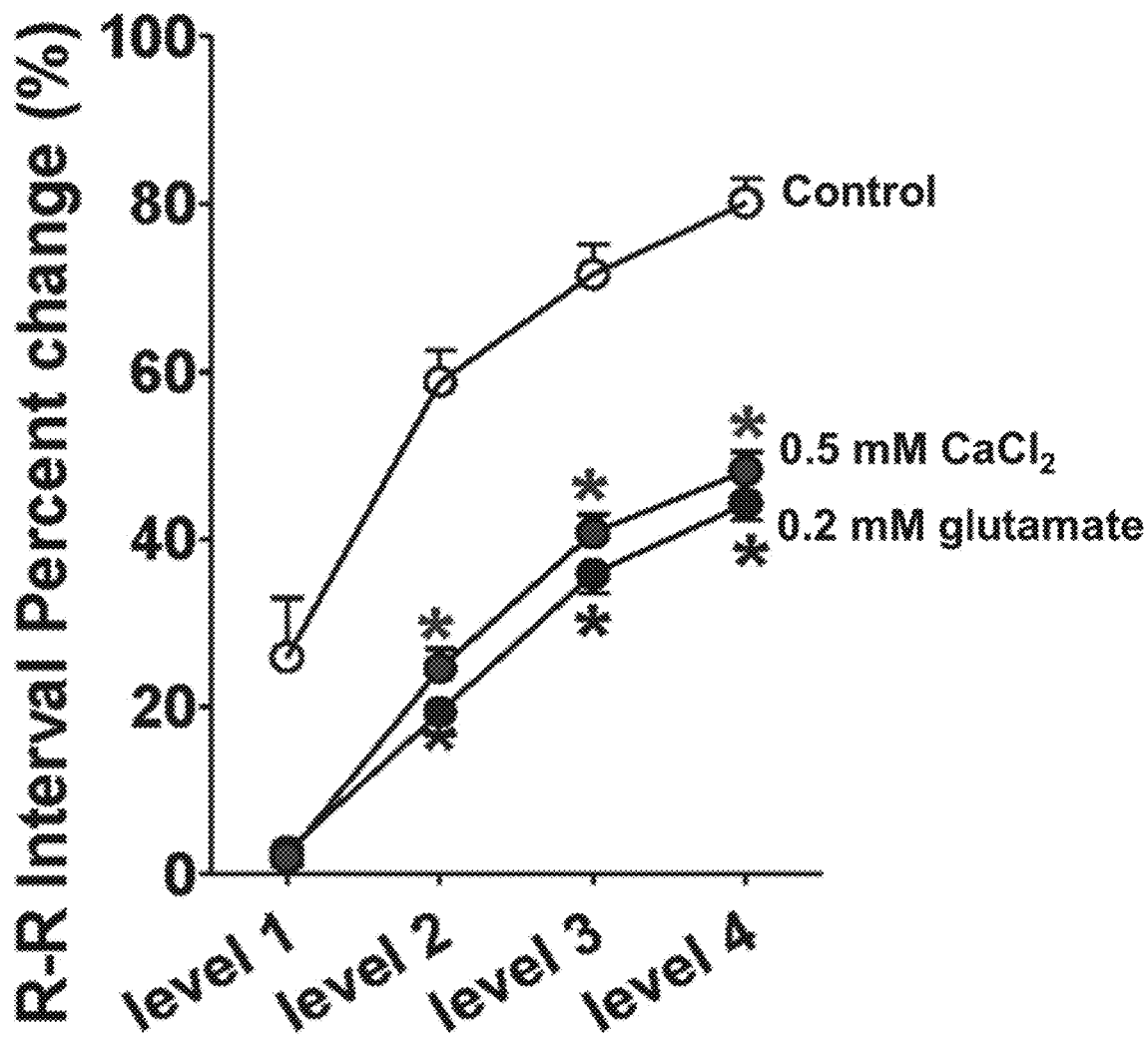

GLUTAMATE TREATMENT OF CARDIOVASCULAR DISORDERS

CROSS-REFERENCE TO RELATED APPLICATIONS/INCORPORATION BY REFERENCE STATEMENT

The present application is a continuation-in-part of U.S. Ser. No. 14/104,422, filed Dec. 12, 2013, now U.S. Pat. No. 9,744,235, issued Aug. 29, 2017; which claims benefit under 35 U.S.C. § 119(e) of U.S. Provisional Application Ser. No. 61/836,392, filed Jun. 18, 2013. The '422 application is also a continuation-in-part of U.S. Ser. No. 12/907,806, filed Oct. 19, 2010, now U.S. Pat. No. 8,740,872, issued Jun. 3, 2014. The entire contents of each of the above-referenced patents and patent applications are hereby expressly incorporated herein by reference.

BACKGROUND

Many cardiovascular diseases are caused by the hyperactivity of the autonomic nervous system (ANS), including such disorders as cardiac arrhythmias including (but not limited to) atrial and ventricular fibrillation and tachycardia, vasovagal syncope, inappropriate sinus tachycardia, and hypertension. Atrial fibrillation (AF) is the most common cardiac arrhythmia requiring treatment and frequently progresses from paroxysmal AF to permanent AF. AF accounts for nearly 20% of the strokes in the U.S. AF inflicted approximately 2.3 million Americans in 2004 and costs the health care system nearly $12 billion a year to treat AF and AF-related strokes. By the year 2050, the number of AF patients is projected to increase to 16 million as the population ages. Nearly half of AF patients are refractory (i.e., do not respond) to anti-arrhythmic drugs and require non-pharmacologic treatment, i.e., surgical or catheter ablation. Clinical trials aimed at ablative treatment of AF resulted in a <50% success rate after five years of follow-up. Standard catheter or surgical ablation procedures produce lesion sets to isolate the pulmonary vein (PV)-atrial junction, containing the presumed triggers and/or substrate for AF. However, in a single procedure, PV antrum isolation only leads to less than 50% success at 5 years for the earliest stage of AF (paroxysmal AF) and approximately 30% for more persistent forms of AF. This approach, widely practiced worldwide, has many drawbacks including a relatively low success rate and various complications, including PV stenosis, cardiac tamponade, esophageal injury, and minor or major strokes. Despite all the advances in ablation technologies in the past 12 years, success of AF ablation has not improved. The unsatisfactory efficacy of AF ablation is mainly due to insufficient understanding of the electrophysiological mechanism(s) underlying the initiation of AF and its progression into more persistent forms of AF. A mechanistically-based therapy is still lacking.

Prior studies of AF initiation in patients and animals indicate that (unbalanced) activation of both sympathetic and parasympathetic nervous systems often precede AF onset. Mammalian hearts are dually innervated by the extrinsic and intrinsic cardiac autonomic nervous system (CANS). It is known that the intrinsic CANS is a neural network composed of many ganglionated plexi and interconnecting nerves and/or neurons. In this neural network, bilateral autonomic inputs come together at many "integration centers" before giving rise to final common pathways that control cardiac rhythm and force of contraction. These intrinsic integration centers are located in epicardial ganglionated plexi (GP) or ligament of Marshall which are overlain by epicardial fat pads. In mammalian hearts, the ligament of Marshall and four major atrial GP (anterior right GP, ARGP; inferior right GP, IRGP; superior left GP, SLGP; and inferior left GP, ILGP) are located adjacent to the junction of the atrium and four pulmonary veins. Stellate ganglia, the gateway of sympathetic innervation to the heart, are located just above the apex of the lung. In previous studies, the inventors have shown that electrical stimulation or injection of acetylcholine into the GP near the PV-atrial junction can initiate sustained AF arising from the PV-atrial junction. Ablation of the four major atrial GP and ligament of Marshall markedly suppressed the inducibility and maintenance of AF in multiple animal models, including the rapid atrial pacing model. Notably, the lesion sets of a standard RF ablation (PV antrum isolation) involve ablation of three of the four major atrial GP, the ligament of Marshall, and numerous autonomic nerves, indicating that autonomic denervation is a major contributor to the antiarrhythmic effects of AF ablation. Importantly, ablations involving only the major atrial GP, without PV antrum isolation, yielded similar results to the standard PV antrum isolation but produced significantly less collateral damage to the atrial myocardium and possibly less consequent iatrogenic left atrial flutter. While re-innervation may occur 3-6 months after RF catheter ablation procedures, the clinical benefits of GP ablation lasted 16-18 months, suggesting that permanent injury to the autonomic neurons in intrinsic CANS may underlie the therapeutic effects of ablation, because unlike nerves, neurons seldom regenerate.

Targeted drug delivery is an increasingly used nanomedicine technology in which delivery of therapeutics to target tissues may increase drug efficacy, eliminate side effects, and reduce costs. Polymeric nanoparticles whose diameters can range from 10-300 nanometers can be formulated as nanocomposites with encapsulated drugs for burst and controlled release. Superparamagnetic nanoparticles, approved in the early 1990s for clinical magnetic resonance imaging enhancement, can be encapsulated in polymers, silicon, or carbohydrates and pulled into tissues to produce more precise lesion sets, thereby reducing non-specific damages.

Standard ablation procedures require the creation of two circumferential lesions to isolate the antrum of all the PVs. Currently, atrial ablation strategies focus on isolating and/or destroying atrial tissue that presumably is responsible for AF, although the long-term consequences of extensive damage to the atrial myocardium, neural elements, and atrial contractility are yet to be discovered.

Multiple basic science studies have demonstrated a significant impact on AF after the major left atrial GPs were ablated. Using a rapid atrial pacing model, Lu et al. (*Cardiovas. Res.*, 84:245-52 (2009); the entire contents of which are hereby expressly incorporated herein by reference) showed that shortening of the effective refractory period (ERP) and an increase of ERP dispersion, as well as increased AF inducibility caused by rapid atrial pacing for 3 hours, were all reversed by ablation of the 4 major atrial GP and the ligament of Marshall (LOM). In animals receiving GP ablation first, rapid atrial pacing for 6 hours failed to change the ERP, ERP dispersion, and AF inducibility. Other animal studies also demonstrated that after ablation of the GP and LOM, AF became more difficult to initiate and sustain. AF often terminated after GP ablation. The inventors proposed that autonomic denervation may serve as a therapeutic modality to prevent paroxysmal AF to progress to more persistent forms of AF. Several clinical studies have indicated the benefits of autonomic denervation by targeting the major atrial GPs identified by high frequency stimulation. When GP ablation was combined with PV isolation, the success rate is significantly better than PV isolation alone. A series of recent manuscripts (Katritsis et al., *Journal of American College of Cardiology*, 62(24):2318-2325 (2013); Pokushalov et al., *Heart Rhythm*, 6:1257-64 (2009); and Pokushalov et al., *Europace*, 12:342-346 (2010); the entire contents of each of which are hereby expressly incorporated herein by reference) also reported similar success rates in AF ablation targeting only the major atrial GPs, in comparison to the standard PV isolation approach.

As noted, clinical studies demonstrated that GP ablation as an adjunct therapy to PV isolation improved the outcome of AF ablation, whereas GP ablation alone produced a success rate similar to the standard PV isolation. This denervation-only ablation strategy has the advantage of producing more focused lesion sets and potentially carrying a smaller risk of producing iatrogenic macro-reentrant left atrial tachycardia.

A method of direct (targeted) treatment of specific portions of the ANS for the inhibition of various disorders, such as (but not limited to) cardiovascular disorders involving the ANS, particularly for permanent inhibition of those portions of the ANS, would be highly desirable.

BRIEF DESCRIPTION OF THE DRAWINGS

Several embodiments of the present disclosure are hereby illustrated in the appended FIGURE. It is to be noted, however, that the appended FIGURE only illustrates certain embodiments and is therefore not intended to be considered limiting of the scope of the inventive concepts disclosed herein.

FIG. 1 shows the effects of calcium and glutamate on heart rate in dogs. Glutamate (0.2 mM) or $CaCl_2$ (0.5 mM) was injected into ganglionated plexi of dogs. The GP were then stimulated after treatment. Levels 1-4 refer to progressively higher stimulation intensity (volts) delivered to GP after injection. Level 1: 10-30 volts; level 2: 40-50 volts; level 3: 60-70 volts; and level 4: 80-90 volts. In the control, as stimulation (voltage) intensity increased, the time interval between R peaks in the QRS waveform (heart rate) increased, indicating a slower heart rate. After glutamate or $CaCl_2$ was injected into the GP, the magnitude of R—R prolongation (heart rate) induced by GP stimulation was markedly suppressed.

DETAILED DESCRIPTION

Preventing glutamate-induced neurotoxicity (excitotoxicity) has been a focus of research and technology development to reduce brain injury caused by a cerebral stroke because glutamate-induced excitotoxicity is well-known to expand the brain injury after a cerebral stroke. In sharp contrast, the compositions and methods of the present disclosure utilize the phenomenon of glutamate-induced excitotoxicity to selectively injure certain hyperactive autonomic neurons underlying diseases such as (but not limited to) atrial fibrillation, syncope, and ventricular tachyarrhythmias. Glutamate (and optionally certain other compounds) can be delivered to a targeted portion of the autonomic nervous system (ANS) such as, but not limited to, cardiac GP or other autonomic ganglia by direct injection into the targeted portion of the ANS of glutamate-containing compounds, compositions, or magnetic nanoparticles, or by magnetic navigation of glutamate-containing magnetic nanoparticles (MNPs). The compositions and methods of the present disclosure therefore relate to targeted therapeutic delivery systems and methods to treat cardiovascular disorders, and in particular (but not by way of limitation), to the use of glutamate to denervate specific targeted portions of the ANS for treating cardiovascular disorders involving the autonomic nervous system.

Before further describing various embodiments of the compositions and methods of the present disclosure in more detail by way of exemplary description, examples, and results, it is to be understood that the embodiments of the present disclosure are not limited in application to the details of compositions and methods as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

All of the compositions and methods of production and application and use thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the methods described herein without departing from the concept, spirit, and scope of the inventive concepts as described herein. All such similar substitutions and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent, patent application, or non-patent publication was specifically and individually incorporated herein, particularly, as noted above, U.S. Ser. No. 14/104,422; U.S. Ser. No. 12/907,806; and U.S. Ser. No. 61/836,392 (each of which incorporated supra).

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the compositions and methods of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment and are not necessarily limited to a single or particular embodiment. In addition, the use of the terms "one embodiment" and "an embodiment" are not to be construed as limiting in any matter of the scope of the present disclosure.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example (but not by way of limitation), 1-10, 10-20, 20-30, 30-40, 40-50, 50-60, 60-75, 75-100, 100-150, 150-200, 200-250, 250-300, 300-400, 400-500, 500-750, 750-1,000, and includes ranges of (for example, but not by way of limitation) 1-20, 10-50, 50-100, 100-500, and 500-1,000. The range 300 nm to 2500 nm therefore refers to and includes all values or ranges of values, and fractions of the values and integers within said range, including for example (but not by way of limitation) 400 nm to 2250 nm, 400 nm to 2000 nm, 600 nm to 2250 nm, 600 nm to 2000 nm, 400 nm to 1750 nm, 750 nm to 2000 nm, 750 nm to 1750 nm, 750 nm to 1600 nm, 400 nm to 1600 nm, and 800 nm to 1200 nm. Any two values within the range of 300 nm to 2500 nm therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation, and/or allergic response commensurate with a reasonable benefit/risk ratio.

By "biologically active" is meant the ability to modify the physiological system of an organism without reference to how the active agent has its physiological effects.

As used herein, "pure," "substantially pure," or "isolated" means an object species is the predominant species present (i.e., on a molar basis, it is more abundant than any other object species in the composition thereof), and particularly, a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein, the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein, the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer to a warm blooded animal, particularly a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments. "Prevention" refers to prophylactic treatment measures to stop a condition from occurring. The term "treating" refers to administering the composition to a patient for therapeutic purposes, and may result in an amelioration of the condition or disease.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation, and/or allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition or consequences of the condition in a subject.

A decrease or reduction in worsening, such as stabilizing the condition, is also a successful treatment outcome. A therapeutic benefit therefore need not be complete ablation or reversal of the condition, or any one, most, or all adverse symptoms, complications, consequences, or underlying causes associated with the condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition (e.g., stabilizing) over a short or long duration of time (e.g., seconds, minutes, hours).

As noted above, the compositions and methods of the present disclosure relate to targeted therapeutic delivery systems and methods of treating cardiovascular disorders, and in particular, use of targeted glutamate to induce a neurotoxicity and/or denervate specific portions of the ANS for treating cardiovascular disorders involving the ANS.

Where used herein, the term "neurotoxicity" refers to a permanent partial or complete loss of neural activity in a targeted portion of the ANS.

Targeted drug delivery is an emerging technology in which therapeutic delivery to tissues can increase drug efficacy, alleviate side effects, and reduce costs. In certain embodiments, polymeric nanoparticles can be formulated with absorbed, adsorbed, attached, embedded, or encapsulated drugs for burst and controlled release. In the present disclosure, targeted delivery of glutamate into an ANS target (such as (but not limited to) by intravenous injection of glutamate-containing magnetically-targeted particles (MNPs), or by direct injection of a glutamate-containing compound, composition, or MNPs) is used to treat various cardiovascular disorders, such as but not limited to, arrhythmias.

Thus, at least one embodiment of the present disclosure includes a method for targeted delivery of a therapeutic agent to specific areas of the ANS including, but not limited to, portions of the intrinsic cardiac autonomic nervous system such as the atrial ganglionated plexi (GP), ligament of Marshall, or the left and right stellate ganglia. The therapeutic agent comprises, in at least one embodiment, glutamate as a free acid (glutamic acid), ionic glutamate, and/or a dissolvable glutamate salt (all referred to herein collectively as "glutamate," "glutamate compound," or "glutamate payload").

The therapeutic agent may further comprise ionic calcium or a calcium salt. For example (but not by way of limitation), the therapeutic agent may comprise calcium diglutamate. Other non-limiting examples of glutamate salts include glutamate salts of sodium, potassium, ammonium, and magnesium. The therapeutic agent may comprise glutamate and a calcium salt able to release $Ca^{2+}$ ions, such as (but not limited to) calcium chloride ($CaCl_2$), calcium carbonate ($CaCO_3$), calcium citrate, calcium gluconate, calcium formate, calcium citrate malate, calcium bis-glycinate, calcium lactate, calcium orotate, calcium fumarate, calcium fluoride, calcium ascorbate, calcium succinate, and calcium aspartate, as well as any combination thereof.

The present disclosure is directed to a new therapy in which glutamate is delivered to hyperactive neural tissues in order to treat diseases, particularly cardiovascular diseases, known to be caused by hyperactive neural tissues. The methods of the present disclosure utilize the binding of glutamate to N-methyl-D-aspartate (NMDA) receptors on the cell membrane of neural tissue. NMDA receptors respond to glutamate, an amino acid, leading to opening of the cell membrane ion channels to allow $Ca^{2+}$ ion influx. Too much glutamate kills the neurons (excitotoxicity) due to excessive concentration of intracellular $Ca^{2+}$. Therefore, exogenously-supplied calcium and/or exogenously-supplied glutamate can exert similar therapeutic effects.

FIG. 1 illustrates that calcium and glutamate have similar effects on the suppression of canine cardiac hyperactive GP function. A low concentration of glutamate is applied to the neural tissue to open the ion channels to allow more $Ca^{2+}$ to enter the neurons, causing their death. FIG. 1 summarizes the results of 4 experiments. Levels 1-4 refer to progressively higher stimulation intensity (volts) delivered to GP. The level of stimulation was: level 1: 10-30 volts; level 2: 40-50 volts; level 3: 60-70 volts; and level 4: 80-90 volts. In the control, as stimulation (voltage) intensity increased, the interval between R peaks in the QRS waveform (heart rate) increased, indicating a slower heart rate. After glutamate (0.2 mM) or $CaCl_2$ (0.5 mM) was injected into the GP, the magnitude of R—R prolongation induced by GP stimulation was markedly suppressed. Glutamate and $CaCl_2$ both had very similar effects on suppression of heart rate. Glutamate and $CaCl_2$ were obtained from Sigma Aldrich (St. Louis, Mo.).

In addition to the results summarized in FIG. 1, previous work showed that calcium-induced apoptosis of the atrial GP (such as, but not limited to, via magnetically-targeted, magnetically-susceptible nanoparticles delivering calcium ions) can effectively inhibit or stop the activity of GP, ligament of Marshall, or the left and right stellate ganglia and the related cardiovascular diseases thereto without permanent damage to other portions of the intrinsic CANS or to myocardium (see parent U.S. Pat. No. 9,744,235, incorporated supra). Without wishing to be bound by theory, it is believed that the exogenously-supplied glutamate of the presently disclosed method has its therapeutic effect by enhancing uptake of endogenous or exogenously-supplied calcium.

More particularly, the glutamate (and other optional components) used in the compositions and methods of the present disclosure may be provided as a payload of nanoparticles (which in one embodiment are magnetic) or other targeted drug delivery systems to injure (i.e., cause a neurotoxicity in) neural tissues in order to treat cardiovascular diseases that are caused by hyperactivity of the autonomic nervous system. In one embodiment, a glutamate compound is provided in a magnetic nanoparticle (MNP), comprised of polymer encapsulant, iron-containing smaller core nanoparticles and the therapeutic payload (i.e., the glutamate compound). In non-limiting embodiments, the MNPs may be administered in dosages in a range of from about 0.01 mg to about 100 mg, in a range of from about 0.1 mg to about 10 mg, or in a range of from about 0.5 mg to about 2.5 mg.

As noted previously, increased intracellular calcium is toxic to cells, and in particular, neurons. Higher than normal calcium ion concentrations have been viewed as a "toxin" to neural tissues. The therapeutic agent(s) disclosed herein utilizes the property of calcium-mediated neurotoxicity to mitigate and/or eliminate the abnormally high neural activity that leads to cardiovascular diseases such as, but not limited to, hypertension, vasovagal syncope, and cardiac arrhythmias. The nanoparticles described or enabled herein may be administered to the subject in the form of compositions in which the nanoparticles are disposed in a pharmaceutically-acceptable carrier or vehicle. Non-limiting examples of pharmaceutically-acceptable carriers or vehicles that may be used in accordance with the present disclosure include, but are not limited to, saline, phosphate-buffered saline, or any other such carrier or vehicle known in the art for such purposes.

The compositions and methods described herein have wide commercial applications since calcium is cationic, regulated, and naturally present in humans. The amount of calcium needed to injure a discrete area of neural tissue may be only a few milligrams in order to reach a local concentration of 5 mM, far below the amount of daily calcium intake (>500 mg) recommended to prevent osteoporosis. In certain embodiments, the amount of calcium needed to injure a discrete area of neural tissue (e.g., 0.1 to 4 $cm^2$) may be only a few milligrams.

In the present disclosure, glutamate, and optionally a calcium compound which releases $Ca^{2+}$ ions, is used as the payload in a targeted drug-delivery system, such as but not limited to, nanoparticles (magnetic or non-magnetic), liposomes, dendrimers, or any other type of drug-delivery system capable of functioning as described herein. After the vehicles of delivery are navigated to the targets (e.g., via cannulation, catheterization, or magnetism), the payload (i.e., glutamate) will be released and incorporated by the targeted cell(s), and the intracellular calcium concentration in the targeted cell(s) will increase substantially. Elevated intracellular calcium subsequently activates a series of enzymes and eventually causes cellular injury and death of the cell by apoptosis.

Atrial fibrillation, one example of a cardiovascular disorder, is the most commonly encountered cardiac arrhythmia and affects 2.5 million people in the United States alone. As the population ages, the incidence is projected to increase to 16 million by the year 2050, a significant portion of whom will have drug-refractory AF and require ablation. Catheter or surgical ablation carries significant risks of serious complications and is very costly. Targeted drug delivery as described in the present disclosure provides a less invasive and less expensive therapeutic modality. With the advances in stereotactic localization by an externally applied magnetic field, it is possible to target (i.e., deliver selectively) the compositions of the present disclosure (such as, but not limited to, MNPs) to one or more GPs, ligament of Marshall, or stellate ganglia to achieve autonomic denervation and treat AF without the risks of serious complications associated with catheter or surgical ablation or the side effects associated with long-term anti-arrhythmic therapy.

Embodiments of the methods of the present disclosure which utilize exogenously-supplied glutamate to a particular site include, but are not limited to:

(1) Treatment of atrial fibrillation and syncope: The targets are the plurality of clusters of cardiac autonomic neurons, including interneurons and neurons in the GP that provide the neural control of cardiac electrophysiology, vascular tone, and contractility. Hyperactivity of these ganglionated plexi leads to hyperactivity of much of the cardiac autonomic nervous system and can cause atrial fibrillation and syncope. A standard coronary angiogram catheter is cannulated into the coronary artery supplying the plurality of ganglionated plexi. In the presence of focused electromagnetic force, magnetic nanoparticles are slowly infused into the coronary artery. Magnetic nanoparticles carrying the glutamate (and/or calcium) payload are conveyed by the microcirculation to the targeted ganglionated plexi and release the payload to cause neurotoxicity.

(2) Treatment of hypertension: The targets are the sympathetic nerves and neurons that control blood pressure, particularly the ones surrounding the renal arteries. An angiogram catheter suitable for size of the targeted artery is selectively engaged into the artery supplying the sympathetic neurons or nerves. The electromagnetic force focuses on the targeted sympathetic nerves or neurons, and magnetic nanoparticles carrying the glutamate payload are slowly infused into the artery and navigate to the targeted neural tissues to release the glutamate to cause neurotoxicity. In the case of renal sympathetic denervation, the renal artery is cannulated to allow the glutamate to engender denervation of the renal sympathetic nerves and neurons.

(3) Treatment of ventricular tachycardia/fibrillation: Ventricular tachycardia/fibrillation, the leading cause of sudden death, is often triggered by high sympathetic activity. The ventricles receive sympathetic innervation from the left and right stellate ganglia as well as their major branches, the ventromedial cardiac nerve and the ventrolateral cardiac nerve, all of which can be selectively injured by the presently described target drug delivery therapy. One of the most suitable targets for sympathetic denervation by targeted drug therapy is to denervate the ventrolateral cardiac nerve (VLCN). This nerve (VLCN) travels within the vein of Marshall, which can be selectively cannulated through the right atrium and coronary sinus. When the magnetic nanoparticles are slowly infused into the vein of Marshall, the electromagnet can sequentially focus on different segments of the vein of Marshall to denervate the entire vein of Marshall and the VLCN within it. Denervation of the VLCN leads to long-term suppression of catecholamine release at the left ventricle, thereby eliminating the triggers for ventricular tachycardia/fibrillation.

(4) Treatment of inappropriate sinus tachycardia: Inappropriate sinus tachycardia (IST) is a very vexing disease resulting from hyperactivity of the sympathetic tone. In the resting state, the sinus rate is often faster than 100 beats per minutes. With minimal exertion, the sinus rate quickly increases to 130-150 beats per minute. This disease is often refractory to pharmacological therapy. The result of catheter ablation was so poor that it is rarely performed today. The right stellate ganglion and ARGP as well as the interganglionic nerve between the two ganglia have been shown to underlie the sinus tachycardia. In the presence of focused electromagnetic force, magnetic nanoparticles as presently described are slowly infused into the arteries supplying the right stellate ganglion or ARGP. Magnetic nanoparticles of the present disclosure carrying the glutamate payload navigate to the targeted ganglionated plexi and cause neurotoxicity.

In certain embodiments, the glutamate is supplied independently of a nanoparticle delivery form, as a glutamate solution in a liquid vehicle or carrier. In certain embodiments, the glutamate is supplied in a non-magnetic nanoparticle delivery form and is injected directly into a targeted portion of the ANS.

In certain embodiments, the present disclosure includes methods for directly injecting glutamate and/or $Ca^{2+}$ into the targeted neural tissue or applying glutamate-containing MNPs, via the vascular system, and targeting them to one or more of the four ganglionated plexi and/or the ligament of Marshall on the epicardial surface of the heart, thus allowing release of the glutamate to cause permanent neuropathy (injury) to the site of action. Additionally, the embolization of the microcirculation by the MNPs may also cause ischemia and subsequent selective temporary or permanent neuropathy of autonomic neurons in the GP. Additionally, the alternating electromagnetic oscillation of the MNPs optionally will allow for controlled warming and thus controlled release of the bioactive agent by elevating the temperature of the MNPs, thereby causing swelling or contraction of a matrix component of the MNPs.

As described elsewhere herein, MNPs used herein generally comprise a biocompatible polymeric matrix component which contains one or more magnetically-susceptible core particles (such as, but not limited to, iron oxides). The MNPs also contain and transport the glutamate (and optionally calcium) compound. The biocompatible polymeric matrix component may be biodegradable. The biocompatible polymeric matrix component may contain the glutamate compound (and optionally calcium). In non-limiting embodiments, the nanoparticles formed by the matrix component, magnetically-susceptible core particles, and glutamate typically have diameters in a range of from about 100 to about 500 nm.

For example, MNPs in various embodiments may have major diameters in the range of about 100 nm to about 110 nm, about 110 nm to about 120 nm, about 120 nm to about 130 nm, about 130 nm to about 140 nm, about 140 nm to about 150 nm, about 150 nm to about 160 nm, about 160 nm to about 170 nm, about 170 nm to about 180 nm, about 180 nm to about 190 nm, about 190 nm to about 200 nm, about 200 nm to about 210 nm, about 210 nm to about 220 nm, about 220 nm to about 230 nm, about 230 nm to about 240 nm, about 240 nm to about 250 nm, about 250 nm to about 260 nm, about 260 nm to about 270 nm, about 270 nm to about 280 nm, about 280 nm to about 290 nm, about 290 nm to about 300 nm, about 300 nm to about 310 nm, about 310 nm to about 320 nm, about 320 nm to about 330 nm, about 330 nm to about 340 nm, about 340 nm to about 350 nm, about 350 nm to about 360 nm, about 360 nm to about 370 nm, about 370 nm to about 380 nm, about 380 nm to about 390 nm, about 390 nm to about 400 nm, about 400 nm to about 410 nm, about 410 nm to about 420 nm, about 420 nm to about 430 nm, about 430 nm to about 440 nm, about 440 nm to about 450 nm, about 450 nm to about 460 nm, about 460 nm to about 470 nm, about 470 nm to about 480 nm, about 480 nm to about 490 nm, or about 490 nm to about 500 nm, as well as any combination thereof, such as, for example, about 130 nm to about 250 nm.

The magnetically-susceptible core particles may be constructed of any material capable of functioning in accordance with the present disclosure. Non-limiting examples of materials from which the particles may be constructed include $Fe_3O_4$ (magnetite), gamma-$Fe_2O_3$ (maghemite), alpha-$Fe_2O_3$ (hematite), FeNi, FePt, and/or Fe—CoNi alloy. In one embodiment, the magnetically-susceptible core particles of the MNPs are superparamagnetic; that is, they are non-magnetic unless exposed to (placed within) an external magnetic field. Typically, the magnetically-susceptible core particles have diameters in the range of about 10 nm to about 15 nm.

In one embodiment, the glutamate, glutamate nanoparticles, or glutamate MNPs of the present disclosure are magnetically targeted to one, two, three, or four of the major atrial GP in the heart. This approach is designed to cause apoptosis and death of the one or more GPs so as to cease the vicious cycle of atrial remodeling, which allows AF to perpetuate itself. Further, using this approach, collateral damage to the surrounding atrial myocardium and intrinsic CANS is minimized. The targeting approach described herein is safer and substantially less expensive than catheter or surgical ablation, preventing the progression from paroxysmal to persistent AF, which carries much higher risks of morbidities such as stroke. In one embodiment, a focused external magnetic field and gradient is used to concentrate intravascularly-injected MNPs in one or more of the major atrial GP to treat patients with AF. Where the MNPs are described herein as being targeted to a GP, it is intended to refer to targeting MNPs to a portion or region of the heart which contains the GP, as well to refer to specifically targeting the GP itself. Further, where the treatment is described as applying a magnetic field and gradient to the GP, it is intended to refer to applying a magnetic field and gradient to a portion or region of the heart which contains the GP, as well as to refer to applying the magnetic field and gradient specifically to the GP itself.

As described herein, in one non-limiting embodiment, the goal is targeted glutamate delivery to the GP in order to treat AF. MNPs are synthesized or provided that contain: (1) a matrix component (which may optionally be thermolabile), (2) one or more magnetically-susceptible core particles (superparamagnetic particles) disposed within the matrix component, and (3) a glutamate payload. The glutamate payload may be disposed within the matrix component (which contains the magnetically-susceptible core particles) or may be present as a separate layer or "shell" over the matrix component (which contains the magnetically-susceptible core particles). In the presence of an external magnetic field, this construct enables magnetic capture of the MNPs at the targeted GP site and allows the glutamate to be released from the MNPs into the epicardial site to ablate the neural elements in the GP.

One non-limiting embodiment of the nanoparticles comprise: (a) poly(lactic-co-glycolic acid) (PLGA) or other polymeric material described herein as a matrix component, (b) magnetically-susceptible core particles, such as magnetite, which are disposed within the matrix component, and (c) an ionizable glutamate compound (and optionally calcium) which is releasably incorporated into the matrix component or is disposed in a layer or shell over or beneath the matrix component.

In certain embodiments, the present disclosure includes methods for the in vivo delivery of a glutamate compound to the heart. In the method, a pharmaceutical composition is provided that contains superparamagnetic, targetable MNPs or non-magnetic particles disposed in a pharmaceutically-acceptable carrier or vehicle (such as, but not limited to, a vehicle suitable for injection). The pharmaceutical composition is administered to a patient by any method known in the art that allows the pharmaceutical composition to function in accordance with the present disclosure; in one non-limiting embodiment, the pharmaceutical composition is injected into the patient. After administration of the pharmaceutical composition, a magnetic field and gradient of appropriate strength and magnitude sufficient to guide and retain a portion of the MNPs at a site of interest, such as but not limited to one or more GPs of the heart, is established.

As used herein, the term "pharmaceutically acceptable" refers to those properties and/or substances which are acceptable to the patient from a pharmacological/toxicological point of view, including bioavailability and patient acceptance, or are acceptable to the manufacturing chemist from a physical-chemical point of view regarding composition, formulation, stability, and isolatability thereof. Phosphate-buffered saline (PBS) is one non-limiting example of a pharmaceutically acceptable carrier or vehicle. Suitable injectable solutions include, but are not limited to, intravenous, subcutaneous, and intramuscular injectable solutions. Non-limiting examples of injectable forms include solutions, suspensions, and emulsions. Other pharmaceutically acceptable carriers include, but are not limited to, Ringers solution, dextrose solution, or other aqueous carrier known in the art. Appropriate non-aqueous carriers may also be used, and non-limiting examples thereof include cyclodextrins (such as, but not limited to, hydroxypropyl beta cyclodextrin), mixed oils (such as, but not limited to, vitamin E oil), polyethylene glycol, and ethyl oleate. One particular non-limiting carrier that may be utilized in accordance with the present disclosure includes cyclodextrin in water. In some embodiments, additives are included in the carrier, such as but not limited to, buffers, preservatives, and other substances that enhance isotonicity and chemical stability.

The components of the MNP may be present at any concentration that allows the MNPs to function in accordance with the present disclosure. In non-limiting exemplary MNPs, the glutamate compound may be present in a range of from about 1% to about 75% by weight, the magnetic core particles may be present in a range of from about 5% to about 50% by weight, and the matrix component may be present in a range of from about 5% to about 90% by weight.

The term "matrix component" as used herein is meant to include any synthetic and/or natural polymeric material which is biocompatible and that can be used in vivo as the matrix which surrounds and/or contains the magnetically-susceptible core particles. Similarly, the matrix component may also contain the glutamate compound (and optionally the calcium compound), or the matrix component may only contain the magnetically-susceptible core particles and may be surrounded by a layer or shell comprising the glutamate compound (and optionally the calcium compound). Alternatively, a first matrix component may contain the magnetically-susceptible core particles, and a second matrix component may contain the glutamate compound (and optionally the calcium compound) and may surround the first matrix component as a layer or shell. The polymeric material which comprises the first matrix component may be the same as or different from the polymeric material which comprises the second matrix component.

The matrix component may be bioinert and/or biodegradable. Some non-limiting examples of polymeric materials that may be utilized in accordance with the present disclosure include polylactides, polyglycolides, polycaprolactones, polydioxanones, polycarbonates, polyhydroxybutyrates, polyalkylene oxalates, polyanhydrides, polyamides, polyacrylic acid, polyoxamers, polyesteramides, polyurethanes, polyacetals, polyorthocarbonates, polyphosphazenes, polyhydroxyvalerates, polyalkylene succinates, poly (malic acid), poly(amino acids), alginate, agarose, chitin, chitosan, gelatin, collagen, dextran, proteins, and polyorthoesters, and copolymers, terpolymers, and combinations and mixtures thereof.

The matrix component may be in the form of a hydrogel, which is defined herein as a water-containing polymeric network. The polymers used to prepare hydrogels can be based on a variety of monomer types, such as, but not limited to, those based on methacrylic and acrylic ester monomers, acrylamide (methacrylamide) monomers, and N-vinyl-2-pyrrolidone. Hydrogels can also be based on polymers such as, but not limited to, starch, ethylene glycol, hyaluronan, heparosan, chitose, and/or cellulose. To form a hydrogel, monomers are typically crosslinked with cross-linking agents such as, but not limited to, ethylene dimethacrylate, N,N-methylenediacrylamide, methylene bis(4-phenyl isocyanate), epichlarohydin glutaraldehyde, ethylene dimethacrylate, divinylbenzene, and allyl methacrylate. In addition, hydrogels can be formed from mixtures of monomers and polymers.

Another type of polymeric network used herein as the matrix component can be formed from one or more hydrophobic monomers and/or macromers. Matrices formed from these materials generally exclude water. Polymers used to prepare hydrophobic matrices can be based on a variety of monomer types such as, but not limited to, alkyl acrylates and methacrylates, and polyester-forming monomers such as ε-caprolactone, glycolide, lactic acid, glycolic acid, and lactide. When formulated for use in an aqueous environment, these materials do not need to be crosslinked, but they can be crosslinked with standard agents such as, but not limited to, divinyl benzene. Hydrophobic matrices can also be formed from reactions of macromers bearing the appropriate reactive groups, such as but not limited to, the reaction of diisocyanate macromers with dihydroxy macromers, and the reaction of diepoxy-containing macromers with dianhydride or diamine-containing macromers.

The matrix component, as noted elsewhere herein, may be biodegradable, bioresorbable, bioinert, and/or biostable. Bioresorbable hydrogel-forming polymers are generally naturally occurring polymers such as polysaccharides, examples of which include, but are not limited to, hyaluronic acid, starch, dextran, alginate, heparin, and chitosan; and proteins (and other polyamino acids), examples of which include, but are not limited to, gelatin, collagen, fibronectin, laminin, albumin, and active peptide domains thereof and combinations thereof. Matrix components formed from these materials degrade under physiological conditions, generally via enzyme-mediated hydrolysis.

Bioresorbable matrix components which can be used herein are generally synthetic polymers prepared via condensation polymerization of one or more monomers. Matrix-forming polymers of this type include, but are not limited to, polylactide (PLA), polyglycolide (PGA), poly(lactide-co-glycolide) (PLGA), and polycaprolactone (PCL), as well as copolymers of these materials, polyanhydrides, and poly-ortho esters, and combinations thereof.

Biostable or bioinert hydrogel matrix-forming polymers which can be used herein as the matrix component are generally synthetic or naturally occurring polymers which are soluble in water, matrices of which are hydrogels or water-containing gels. Non-limiting examples of this type of polymer include, but are not limited to, polyvinylpyrrolidone (PVP), polyethylene glycol (PEG), polyethylene oxide (PEO), polyacrylamide (PAA), polyvinyl alcohol (PVA), and combinations thereof.

Biostable or bioinert matrix-forming polymers which can be used herein as the matrix component are generally synthetic polymers formed from hydrophobic monomers, such as but not limited to, methyl methacrylate, butyl methacrylate, dimethyl siloxanes, and the like. These polymer materials generally do not possess significant water solubility but can be formulated as neat liquids which form strong matrices upon activation. It is also possible to synthesize polymers which contain both hydrophilic and hydrophobic monomers.

The matrix component can optionally provide a number of desirable functions or attributes. For example, but not by way of limitation, the polymers can be provided with water soluble regions, biodegradable regions, and/or hydrophobic regions, as well as polymerizable regions.

In particular non-limiting embodiments, the matrix component of the compositions of present disclosure may include any of the following: poly (glycolic acid), poly (DL-lactic acid), poly (lactic acid-co-glycolic acid) copolymer (PLGA), poly ($\epsilon$-caprolactone), the poly (alkylcyanoacrylate) family, poly (isobutylcyanoacrylate), poly (ethylcyanoacrylate), polyethylenimine, poly ($\beta$-aminoesters), quaternary ammonium polysaccharides, poly (N-isopropylacrylamide i.e., PNIPA-Am), poly (N-isopropylmethacrylamide-co-acrylamide) copolymer, polyhydroxybutyrate, poly (ester-amide), poly (methylidene malonate), polyglutaraldehyde, poly (N-isopropylacrylamide)/poly (ethyleneimine) copolymer, PNIPA-Am/poly[N-(2-hydroxypropyl) methacrylamide] copolymer, PNIPA-Am-co-acrylamide-block-polyallylamine copolymer, PNIPA-Am-co-methylmethacrylate-co-methacrylic acid, poly[2-dimethyl(aminoethyl)methacrylate] (PDMAEM), PNIPA-Am/PDMAEM copolymer, PNIPA-Am-co-DMSO copolymer, PNIPA-Am-co-N,N-dimethylaminopropyl acrylamide-co-butylmethacrylate copolymer, poly (methacrylic acid-co-hydroxyethyl methacrylate copolymer, polyvinyl-benzyl-o-$\beta$-galactopyranosyl-D-glucosamide copolymer, Polyethylene glycol (PEG), PEG-silane copolymer, fluidMAG-particles (chemicell GmbH, Berlin, Germany), poly (N,N-dimethylacrylamide), PLURONIC® F127 (BASF Corp., North Mount Olive, N.J.), carboxymethyl dextran, PEGylated amphiphilic triblock copolymer, gum Arabic, gum tragacanth, 2-(acetoacetoxy) ethyl methacrylate, poly (ethylene) glycol methylether methacrylate, chitosan triphosphate, chitosan triphosphate-hyaluronic acid, polyvinyl acetate, poly (vinylpyrrolidone), $SiO_2$-polymethylmethacrylate, poly [oligo(ethyleneglycol)methacrylate-co-methacrylic acid], poly (N-vinylacetamide) (NVA), PNIPAAm-co-NVA copolymer, Dextron-poly ($\epsilon$-caprolactone)-2-hydroxyethyl methacylate-PNIPAAm copolymer, PNIPAAm-PEG copolymer, poly (ethyl-2-cyanocrylate), poly (butylcyanoacrylate), poly (hexylcyanoacrylate), poly (octylcyanoacrylate), heparin compounds, hyaluronic acid, and poly (3-(trimethoxysilyl)propyl methacrylate-r-PEG methyl ether methacrylate-r-N-acryloxysuccinimide), and any combination of the above.

In certain embodiments, one or more appropriate glutamate compounds are incorporated within the matrix component of the MNPs (or in a layer surrounding the matrix component) for delivery to specific sites, for example, under control of a magnetic field. The glutamate compound can be embedded, contained within, coated on, or adsorbed or absorbed on or within the matrix component (such as, but not limited to, a hydrogel or a block copolymer), and permitted to diffuse therefrom at a controlled rate. The rate of diffusion of the glutamate compound can be controlled by varying the composition of the matrix component and/or by varying the magnetic field or gradient as discussed elsewhere herein.

The MNPs produced and utilized as described herein may assume any shape that allows them to function in accordance with the present disclosure. In certain non-limiting embodiments, the MNPs may be in the shape of a cylinder, a cylindrical rod, a worm, a circular disc, a sphere, an ovoid, an irregular shape, or any combination thereof.

In certain embodiments of the present disclosure, once the MNPs have been magnetically drawn to the desired area of the ANS, such as but not limited to, the stellate ganglia, the ligament of Marshall, or one or more of the atrial GP of the cardiac ANS, the magnetic force applied to the MNPs can be changed from static to oscillating (e.g., alternating). This change causes the MNPs to become warmer, above normal physiologic temperatures (i.e., above 37° C.), thereby causing an increase in the release of the glutamate compound from the matrix component of the nanoparticles or MNPs in a phenomenon referred to herein as "magnetothermally-triggered release." This may be induced, for example but not by way of limitation, at about 100 Hz to about 300 Hz.

In regard to the types of magnets which can be used herein, the pole face field strength may be, in one particular non-limiting embodiment, about 0.26 Tesla (T) to about 0.46 T. The magnetic gradient in one non-limiting embodiment is in a range of from about 2 T/meter to about 10 T/meter. When the magnet is an electromagnet, the duty cycle of the electromagnet can range, for example but not by way of limitation, from about 10% to about 33%. Its output can be a square wave or a balanced wave form, equal upward and downward, representing a change in polarity. In regard to the strength of the magnetic field strength to be applied at the MNP capture point in the coronary micro-circulation, one embodiment of a particular range is about 0.1 T to about 0.4 T. Ranges of frequencies of oscillations to be applied include, by way of example but not by way of limitation, from about 100 to about 200 Hz or from about 200 to about 400 Hz for heating of local tissue in the vicinity of the MNPs that were targeted to that site.

In an alternative version of the present disclosure, once the MNPs with the glutamate compound are located in the targeted area of the ANS (such as, but not limited to, neuronal tissue of the heart), neurons may be killed by magnetically heating the MNPs to a temperature at which the neuronal tissue dies. Non-limiting exemplary heated temperatures are in a range from about 49° C. to about 55° C. (where normal physiologic temperature is <38° C.). This can be induced by exposure of the MNPs to a frequency of from about 200 to about 400 Hz, for example.

In general, during a single treatment comprising the method of the present disclosure, the magnetic field and gradient is applied to the specific portions of the ANS for non-limiting, exemplary duration periods of from about 10 minutes to about 6 hours, from about 20 minutes to about 4 hours, and from about 30 minutes to about 2 hours, although it will be understood that the magnetic field or gradient can be applied for other duration periods, and non-limiting duration periods encompassed by the scope of the present disclosure include about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, or about 360 minutes, or any integeric minute there within, such as about 37 or about 152 minutes, or any range of such minutes, such as for example (but not by way of limitation) about 10 to about 60 minutes.

In another embodiment, the magnetic field or gradient is applied to the MNPs for targeting the MNPs in association with concurrent application of Magnetic Resonance Imaging (MRI), for example, in a manner shown in U.S. Published Patent Application No. 2010/0079142, the entire contents of which are expressly incorporated by reference herein.

In one embodiment, the MNPs are administered in a treatment protocol comprising multiple doses, administered simultaneously, consecutively, or sequentially over time. One non-limiting example of a treatment protocol includes a first treatment comprising one or two doses, optionally followed by another treatment in about 6-12 months (e.g., about 6-8 months or about 8-10 months), and optionally followed by one to three similar treatments administered after similar durations of time. In one non-limiting embodiment, the concentration of the glutamate compound of the MNPs is in a range of about 10 ng to about 10 mg per dose, or is in a range of about 100 ng to about 1 mg per dose. In one version of the present disclosure, the magnetic field and gradient applied to the MNPs causes the MNPs to move through the myocardial tissues at a velocity in a range of, but not limited to, about 0.01 to about 0.1 mm/min. In specific embodiments, the velocity may be at least about 0.01 mm/min, at least about 0.02 mm/min, at least about 0.03 mm/min, at least about 0.04 mm/min, at least about 0.05 mm/min, at least about 0.06 mm/min, at least about 0.07 mm/min, at least about 0.08 mm/min, at least about 0.09 mm/min, or at least about 0.10 mm/min, for example.

Additionally, the contractions of the myocardium while the heart is beating also facilitate movement of the drug, and the MNPs, through the myocardium, in the direction of the stronger magnetic field and gradient and down the field and gradient.

Generally, the magnetic field and gradient may be applied externally to the body, on or near the surface of the chest or other area of the ANS to be targeted.

In one embodiment, the magnet or electromagnet pulls the MNP into the region of the ANS (e.g., the cardiac ANS) where body temperature causes the matrix component (e.g., poly NIPA or other thermolabile material) to release the glutamate compound. This heat lability is a property of the particle's matrix component.

As noted above, once the MNPs are pulled into position near the targeted region, e.g., the ganglionated plexi, the electromagnet can be adjusted to present an alternating magnetic field of known frequencies to cause warming of the MNPs by oscillating the magnetite (or other ferrous material in the core), then using the magnet to accelerate the release of the glutamate compound for a controlled release of the therapeutic. Furthermore, the tissue in the vicinity of the ganglionated plexi is warmed by the oscillation of the nanoparticles.

The quantitative denervation, which corrects the autonomic imbalance of neural control of the targeted ANS, may be accomplished both by release of the glutamate compound in the targeted tissue (e.g., the ganglionated plexi such as the ARGP), and additionally (and potentially synergistically) by the embolization of the microvessels serving the targeted site of the ANS. This embolization is caused by magnetic capture and holding of the superparamagnetic nanoparticles carrying the MNPs in the vicinity of the GP so that blood flow thereto is reduced, thereby causing ischemia and subsequent death of neurons in the targeted area.

As noted elsewhere herein, the intrinsic body temperature or magnetic oscillation of the magnetic field or gradient can induce heating of thermolabile forms of the matrix component of the MNPs to the lower critical solution temperature (LCST) of the polymer, thereby inducing release of the glutamate compound into the circulation. The level of heating necessary to reach the LCST can be established by the chemical formulation and determined by a person of ordinary skill in the art. In one embodiment, the LCST of the matrix component is set by its formulation at body temperature, so that when the particles are warmed to about 38° C., they will begin to release the glutamate. This keeps the solution stable at room temperature, and the glutamate will not be released prematurely on the shelf. If warmed to the LCST by magnetic oscillations, the release will be accelerated and under the control of the magnet. If the particles are warmed above the LCST, this will assure that most or all of the glutamate payload is released. It is known that neurons are labile to excessive heat. As noted elsewhere herein, if the tissue in the region of the GP is heated to about 48-50° C., then neurons therein will begin to die (before cardiac cells).

The external source of a magnetic field and gradient of the present disclosure is capable of (i) magnetizing the superparamagnetic particle and (ii) increasing a degree of magnetization of the MNPs and thereby increasing the force of attraction. Those skilled in the art using guidance provided in this disclosure will be able to select the proper magnetic source and its capabilities without undue experimentation. One particular (but non-limiting) external source is an electromagnet.

In one embodiment related to targeting a portion of the ANS of the heart (the intrinsic CANS), catheterization of the heart into the arteries supplying the stellate ganglia, the ligament of Marshall, or GP can be made in the subject and is done readily every day by interventionalists performing angiography of the coronary vessels. Such a catheter can be used to release a dosage of a solution of the MNPs or other glutamate-containing carrier that will flow downstream towards the target cardiac tissue containing a ganglionated plexi desired to be targeted, such as (but not limited to) the anterior right GP (ARGP). At the ARGP, or other GP, a magnetic field and gradient will be present, caused either by a permanent magnet or electromagnet, which is generally located outside of the chest, but in certain embodiments may be placed internally in the chest of a patient.

Specific non-limiting examples of MNPs comprise a composite containing magnetite, a biocompatible, magnetically susceptible iron oxide that is superparamagnetic. The diameters of the magnetically-susceptible core particles in this example are in a range of about 10 to about 15 nm. Single or multiple magnetite particles may be encapsulated in the matrix component to form a single MNP. Thus, when the magnetic particles containing the glutamate are in the region of the GP, they respond to the magnetic field and gradient and are captured in the GP microcirculation subserving the GP; the MNPs are then held there as long as there is a magnetic field and gradient present. Once magnetically captured, the MNPs are pulled from the coronary microcirculation into the epicardium containing the GP (i.e., completion of targeting), toward the pole face of the magnet. Next, the glutamate compound begins to be released and begins to decrease the autonomic neural activity in the GP by causing apoptosis of neural cells.

In one embodiment of the present disclosure, MNPs are synthesized that are made of magnetically-susceptible core particles that include $Fe_3O_4$, a matrix component comprising a thermo-responsive polymeric hydrogel, and the glutamate compound. To synthesize the MNPs, the magnetically-susceptible core particles (e.g., magnetite) are formed by co-precipitation of ferrous and ferric salts in the presence of basic solution and docusate sodium salt as a surfactant. Then, the magnetic nanoparticles are coated with vinyltrimethoxysilane via acid catalyst hydrolysis followed by electrophilic substitution on the surface of the MNP forming a magnetic core. Poly-N-isopropylacrylamide-co-acrylamide (pNIPA-AAm), a thermo-responsive hydrogel, is then polymerized on the magnetic core via a silane coupling agent and radical polymerization method. This process allows a strong attachment of the magnetic core with the polymeric hydrogel matrix component, thereby preventing the magnetically-susceptible core particles of the magnetic core of the MNP from diffusing out of the matrix component and also permitting the encapsulation of a glutamate compound. The lower critical solution temperature (LCST), the temperature above which the hydrogel contracts and disintegrates, is formulated at 37° C., allowing for enhanced calcium release only at body temperature.

Nanoparticles with superparamagnetic properties have attracted clinical attention for drug delivery because of their unique property that they magnetize strongly in the presence of an external magnetic field but retain no permanent magnetism after the magnetic field is removed. Thermoresponsive hydrogels based on pNIPA-AAm have been synthesized and functionalized previously. It is contemplated herein that at temperatures above the lower critical solution temperature (LCST), a pNIPA-AAm hydrogel will shrink by expelling water molecules, thereby releasing the glutamate compounds incorporated in the hydrogel. In one embodiment, the MNPs comprising pNIPA-AAm have a LCST at 37° C.

In one non-limiting example, the composition of MNPs comprises 1 mg/ml of MNPs in solution, which comprise about 30% magnetite (by mass), about 50% of a glutamate compound (by mass), and about 20% of PLGA (by mass). In this embodiment, the magnetite comprises about 300 micrograms/ml, the glutamate comprises about 500 micrograms/ml, and the PLGA comprises about 200 micrograms/ml. The amount of injected MNPs is 1 mg provided in 1 ml of injectate. Up to about 50% to about 75% of the glutamate is released from the PLGA polymer shell within about 2 to about 3 hours, and the remainder is released over a period of days thereafter.

Although embodiments have been described in detail, it should be understood that various changes, substitutions, and alterations can be made herein without departing from the spirit and scope of the present disclosure as defined in the appended claims. Moreover, the scope of the present disclosure is not intended to be limited to the particular examples and embodiments of the process, items of manufacture, compositions of matter, means, methods and steps described in the specification. As one of ordinary skill in the art will readily appreciate from the present disclosure, processes, items of manufacture, compositions of matter, means, methods, or steps, presently existing or later to be developed, that perform substantially the same function or achieve substantially the same result as the corresponding examples and embodiments described herein may be utilized according to the present disclosure. Accordingly, the appended claims are intended to include within their scope such processes, items of manufacture, compositions of matter, means, methods, or steps.

What is claimed is:

1. A method of treating a cardiovascular disorder in a subject in need of such treatment, the method comprising the step of:
administering a glutamate compound to a subject, wherein the glutamate compound is provided as a component of a magnetic nanoparticle and is specifically delivered to a targeted portion of the autonomic nervous system (ANS) of the subject, wherein the glutamate compound leads to a neurotoxicity in the targeted portion of the ANS, thereby treating the cardiovascular disorder in the subject.

2. The method of claim 1, wherein the magnetic nanoparticle is injected directly into the targeted portion of the ANS.

3. The method of claim 1, wherein the magnetic nanoparticle is administered to a vascular component of the subject.

4. The method of claim 3, wherein the vascular component is an artery or a vein.

5. The method of claim 1, wherein the magnetic nanoparticle comprises a biocompatible matrix component within which the glutamate compound is releasably incorporated.

6. The method of claim 1, wherein the targeted portion of the ANS comprises at least one ganglionated plexi.

7. The method of claim 6, wherein the at least one ganglionated plexi is selected from the anterior right ganglionated plexi, the inferior right ganglionated plexi, the superior left ganglionated plexi, the inferior left ganglionated plexi, the ligament of Marshall, the left stellate ganglion, and the right stellate ganglion.

8. The method of claim 1, wherein the targeted portion of the ANS is at least one portion of the ventrolateral cardiac nerves, the vein of Marshall, and the renal arterial sympathetic nerves and neurons that control blood pressure.

9. The method of claim 1, wherein the targeted portion of the ANS is the PV-atrial junction.

10. The method of claim 1, wherein the cardiovascular disorder is at least one of an atrial disorder, a ventricular disorder, vasovagal syncope, a sinus nodal disorder, and hypertension.

11. The method of claim 1, wherein the glutamate compound is selected from the group consisting of glutamic acid, ionic glutamate, calcium diglutamate, magnesium diglutamate, sodium glutamate, potassium glutamate, and ammonium glutamate.

12. A method of treating a cardiovascular disorder in a subject in need of such treatment, the method comprising the step of:
administering a magnetic nanoparticle to a subject, wherein the magnetic nanoparticle is specifically delivered to a targeted portion of the autonomic nervous system (ANS) of the subject, the magnetic nanoparticle comprising:
a biocompatible matrix component containing magnetically-susceptible core particles; and
a glutamate compound; and
wherein the glutamate compound leads to a neurotoxicity in the targeted portion of the ANS when released from the magnetic nanoparticle, thereby treating the cardiovascular disorder in the subject.

13. The method of claim 12, wherein the magnetic nanoparticle is injected directly into the targeted portion of the ANS or is administered to a vascular component of the subject.

14. The method of claim 12, wherein:
the targeted portion of the ANS is selected from the group consisting of at least one ganglionated plexi, the PV-atrial junction, at least one portion of the ventrolateral cardiac nerves, the vein of Marshall, and the renal arterial sympathetic nerves and neurons that control blood pressure; and
the cardiovascular disorder is at least one of an atrial disorder, a ventricular disorder, vasovagal syncope, a sinus nodal disorder, and hypertension.

15. The method of claim 12, wherein the glutamate compound is contained within the biocompatible matrix component and/or is disposed in a layer over the biocompatible matrix component.

16. A method of treating a cardiovascular disorder in a subject in need of such treatment, the method comprising the steps of:
administering a glutamate compound to a subject, wherein the glutamate compound is specifically delivered to a targeted portion of the autonomic nervous system (ANS) of the subject, wherein the glutamate compound leads to a neurotoxicity in the targeted portion of the ANS, thereby treating the cardiovascular disorder in the subject; and
administering calcium to the subject for treating the cardiovascular disorder in concert with the glutamate compound.

17. The method of claim 16, wherein the calcium is administered to the subject with the glutamate compound.

18. The method of claim 16, wherein the calcium is administered to the subject separately from the glutamate compound.

* * * * *